US012661427B2

(12) United States Patent
Huang et al.

(10) Patent No.: US 12,661,427 B2
(45) Date of Patent: Jun. 23, 2026

(54) SELF-ADHESIVE ABSORBABLE BIOLOGICAL PATCH AND PREPARATION METHOD AND USE THEREOF

(71) Applicant: Beijing Biosis Healing Biological Technology Co., Ltd., Daxing District (CN)

(72) Inventors: Yiqian Huang, Daxing District (CN); Pengfei Wei, Daxing District (CN); Wei Jing, Daxing District (CN); Xueqiao Yu, Daxing District (CN); Yan Zhang, Daxing District (CN); Bo Zhao, Daxing District (CN)

(73) Assignee: Beijing Biosis Healing Biological Technology Co., Ltd., Daxing District (CN)

( * ) Notice: Subject to any disclaimer, the term of this patent is extended or adjusted under 35 U.S.C. 154(b) by 497 days.

(21) Appl. No.: 18/555,911

(22) PCT Filed: Sep. 26, 2022

(86) PCT No.: PCT/CN2022/121486
§ 371 (c)(1),
(2) Date: Oct. 18, 2023

(87) PCT Pub. No.: WO2024/000860
PCT Pub. Date: Jan. 4, 2024

(65) Prior Publication Data
US 2024/0238477 A1 Jul. 18, 2024

(30) Foreign Application Priority Data

Jun. 27, 2022 (CN) .......................... 202210743359.2

(51) Int. Cl.
*A61L 24/04* (2006.01)
*A61F 2/00* (2006.01)
(Continued)

(52) U.S. Cl.
CPC .......... *A61L 24/043* (2013.01); *A61F 2/0063* (2013.01); *A61L 15/325* (2013.01);
(Continued)

(58) Field of Classification Search
None
See application file for complete search history.

(56) References Cited

FOREIGN PATENT DOCUMENTS

| CN | 102596275 A | 7/2012 | |
| CN | 106075550 A | * 11/2016 | ............. A61L 27/58 |

(Continued)

*Primary Examiner* — Yi-Shan Yang
(74) *Attorney, Agent, or Firm* — The Dobrusin Law Firm, P.C.

(57) ABSTRACT

In view of the shortcomings of low tissue adhesiveness or low tissue compliance and the problems of about low operability and inadequate convenience and portability of current tissue sealing materials, the present application provides an absorbable biological patch with self-adhesiveness, comprising a substrate layer and an adhesive coating located on the substrate layer, wherein the substrate layer is a biological material, and the adhesive coating is a succinimidyl ester group-grafted polyacrylic crosslinked copolymer, and optionally comprises a biodegradable polymer. The biological patch can be adhered firmly to the tissue surface and applied directly without extra preparation, and has good biocompatibility, has biodegradability, and can be used in common clinical scenarios such as tissue adherence, wound hemostasis, and low-pressure leakage of body fluids.

18 Claims, 3 Drawing Sheets

(51) Int. Cl.

| | | |
|---|---|---|
| *A61L 15/32* | (2006.01) | |
| *A61L 15/40* | (2006.01) | |
| *A61L 15/44* | (2006.01) | |
| *A61L 15/58* | (2006.01) | |
| *A61L 15/64* | (2006.01) | |
| *A61L 24/00* | (2006.01) | |

(52) U.S. Cl.

CPC ............... *A61L 15/40* (2013.01); *A61L 15/44* (2013.01); *A61L 15/585* (2013.01); *A61L 15/64* (2013.01); *A61L 24/0015* (2013.01); *A61L 24/0042* (2013.01)

(56) References Cited

FOREIGN PATENT DOCUMENTS

| | | | | | |
|---|---|---|---|---|---|
| CN | 107050520 | A | | 8/2017 | |
| CN | 210250161 | U | * | 4/2020 | |
| CN | 112007200 | A | | 12/2020 | |
| CN | 112220960 | A | | 1/2021 | |
| CN | 113952500 | A | * | 1/2022 | ............ A61L 24/06 |
| CN | 114306725 | A | | 4/2022 | |
| CN | 114423460 | A | | 4/2022 | |
| WO | 2017/165490 | A1 | | 9/2017 | |
| WO | 2021/237543 | A1 | | 12/2021 | |

* cited by examiner

Blank Control

Self-Adhesive Absorbable
Biological Patch

SELF-ADHESIVE ABSORBABLE BIOLOGICAL PATCH AND PREPARATION METHOD AND USE THEREOF

The present application claims the benefit of a priority of an earlier application filed with the China National Intellectual Property Administration on Jun. 27, 2022, of which the Chinese Patent Application No. is 202210743359.2 entitled "SELF-ADHESIVE ABSORBABLE BIOLOGICAL PATCH AND PREPARATION METHOD AND USE THEREOF". The entire contents of this earlier application are incorporated herein by reference.

TECHNICAL FIELD

The present disclosure relates to the technical field of medical biomaterials, in particular to a self-adhesive absorbable biological patch comprising a substrate layer and an adhesive coating, and a preparation method and medical use thereof.

BACKGROUND

Tissue sealing material is a material used to seal and block damaged areas in time when damage, bleeding, or low-pressure fluid leakage occurs to body tissues.

At present, the predominant tissue sealing materials in the market include a liquid state (such as Braun's Histoacryl products with the main component of butyl-2-cyanoacrylate), a semi-solid state (such as Ethicon's Surgiflo products with the main component of porcine-derived gelatin), and a powder state (such as Baxter's Coseal products with the main component of two modified polyethylene glycol polymers).

The mechanism for Histoacryl α-cyanoacrylate products to produce a tissue adhesive effect is that the monomer undergoes anionic polymerization to form polycyanoacrylate, which adheres to tissues via chemical bonds. The monomer polymerization will release heat, and the monomer has certain biological toxicity, which may burn tissues and endanger the body safety. Consequently, they are somewhat restricted in clinical applications. Besides, when the tissue wound surface is in a wet state, the α-cyanoacrylate products cannot be polymerized to achieve tissue adherence based on their polymerization principle.

In Surgiflo fluid gelatin products, a certain dose of glycerol is added as a thickener. Such kind of semi-solid materials is diluted with normal saline into a slurry form before use and then injected into tissues. On the one hand, the materials generate a tissue adhesive effect by means of hydrogen bonding, etc.; on the other hand, the gelatin component can trigger the mechanism of the cascade reaction of platelet recruitment and body coagulation to play a hemostatic role. For Coseal two modified polyethylene glycol tissue adhesive material, the two kinds of powder are dissolved separately in normal saline or in a phosphate buffer solution before use and then injected into tissues with their specific injection devices to form solid adhesive hydrogels in situ in the tissues, which creates a tissue sealing effect as a means of mechanical closure. Since these products are usually required to be prepared in advance before use and then topically injected or filled into the damaged areas with the dissolved materials, the products cannot be used directly in scenarios such as wound hemostasis. There is no doubt that this process increases the preoperative preparation time and extends the operative treatment time. Furthermore, it is usually necessary to cooperate with specific medical apparatus and instruments to enable these products to be formulated and properly used, which poses certain difficulties and obstacles to the procedures of clinical emergency operations.

Besides, to be a tissue sealing material, problems such as the matching between its mechanical strength and the mechanical strength applied to the tissue and tissue compliance are also required to be considered in addition to adequate tissue adhesiveness.

Therefore, there still remains a need to develop a tissue sealing material with excellent tissue adhesiveness and compliance, and more desirably a ready-to-use tissue sealing material, to provide greater convenience for operative procedures and treatment.

SUMMARY

In view of the shortcomings of low tissue adhesiveness or low tissue compliance of current tissue sealing materials, the present application provides a tissue sealing material with excellent tissue adhesiveness and compliance, which can be firmly adhered to the tissue surface based on the specific tissue adherence mechanism and has appropriate mechanical strength and high tissue compliance. Besides, in view of the problems about low operability and inadequate convenience and portability of current tissue sealing materials, the present disclosure further provides a biological patch that can be used directly for adhering tissues without extra preparation. Additionally, the biological patch has good biocompatibility, has biodegradability, and can be used in common clinical scenarios such as tissue adherence, wound hemostasis, and low-pressure leakage of body fluids.

In the present disclosure, the meaning of "biodegradable" is as same as that of "bioabsorbable" or "absorbable", all of which have a known and generic meaning in the art. That is, the patch materials of the present disclosure can fully exert their functions in the body for a period of time; then they start to degrade and lose their original functions after a period of time, and their degradation products are absorbed or excreted after metabolism, without residues in the body.

The first aspect of the present disclosure provides a self-adhesive absorbable biological patch.

According to the present disclosure, the self-adhesive absorbable biological patch is a bilayer structure comprising a substrate layer and an adhesive coating located on the substrate layer.

According to the present disclosure, the substrate layer is a biological material, which is biodegradable, preferably a biological material substantially containing a collagen protein. The collagen protein may be naturally sourced, synthesized, modified or crosslinked, which includes, but is not limited to, submucosa, dermis, pericardium, collagen, gelatin and the like. In some embodiments of the present disclosure, the substrate layer is small intestinal submucosa, preferably decellularized small intestinal submucosa. In some embodiments of the present disclosure, the substrate layer is dermis, preferably decellularized dermis. In some embodiments of the present disclosure, the substrate layer is pericardium, preferably decellularized pericardium. The submucosa (such as small intestinal submucosa), dermis, and pericardium and the like are preferably derived from mammals, for example, pigs, cattle, sheep, dogs, cats and the like. In one embodiment of the present disclosure, the substrate layer is decellularized porcine small intestinal submucosa.

The substrate layer has a thickness of 0.01 mm to 1 mm, generally 0.05 mm to 0.5 mm, preferably 0.08 mm to 0.3 mm, e.g., 0.08 mm, 0.09 mm, 0.1 mm, 0.11 mm, 0.12 mm, 0.14 mm, 0.16 mm, 0.18 mm, 0.2 mm, 0.24 mm, or 0.26 mm.

The substrate layer may be a homogeneous layer or may be in the form of a laminate formed by two or more separable layers. When the substrate layer is in the form of a laminate, the composition of each of the separable layers may or may not be the same. In one embodiment of the present disclosure, the substrate layer is composed of 2 to 9 layers of the decellularized small intestinal submucosa, for example, composed of 2 layers, 3 layers, 4 layers, 5 layers, 6 layers, 7 layers, 8 layers or 9 layers of the decellularized small intestinal submucosa.

According to the present disclosure, the adhesive coating comprises a succinimidyl ester group-grafted polyacrylic crosslinked copolymer, and further optionally contains an additional biodegradable polymer.

The polyacrylic crosslinked copolymer is formed by polymerizing and crosslinking acrylic acid and/or acrylamide with an acrylated biodegradable polymer and acrylic acid-N-succinimidyl ester, which can absorb water in an aqueous environment to form a gel.

According to the present disclosure, in the succinimidyl ester group-grafted polyacrylic crosslinked copolymer, the weight ratio of acrylic acid and/or acrylamide, the acrylated biodegradable polymer, and acrylic acid-N-succinimidyl ester as three monomers is (50 to 300):(2 to 50):(1 to 50), preferably (200 to 300):(2 to 30):(1 to 20), more preferably (200 to 300):(2 to 10):(1 to 10).

According to the present disclosure, in the adhesive coating, the amount of the succinimidyl ester group-grafted polyacrylic crosslinked copolymer is 4 to 120 mg/cm$^2$, preferably 10 to 80 mg/cm$^2$, more preferably 20 to 40 mg/cm$^2$; and the amount of the biodegradable polymer is 0 to 30 mg/cm$^2$, preferably 1 to 20 mg/cm$^2$, more preferably 5 to 10 mg/cm$^2$.

According to the present disclosure, in the adhesive coating, the weight ratio of the succinimidyl ester group-grafted polyacrylic crosslinked copolymer to the biodegradable polymer is (1 to 8):(0 to 3), preferably (2 to 8):(1 to 3), more preferably (2.7 to 4.3):(1 to 1.5).

According to the present disclosure, the adhesive coating may be loaded with an additional active material including, but not limited to, protein drugs, polypeptides, growth factors, enzymes and the like, or antibacterial or anti-inflammatory drugs, cationic surfactants, polyphenols and the like, or metals and compounds thereof such as magnesium oxide, calcium carbonate and the like. The active material endows the self-adhesive absorbable biological patch with various biological functions and uses. The active material may be present in the adhesive coating by physically mixing, or may be present in the adhesive coating by chemically covalently bonding.

According to the present disclosure, the adhesive coating is in a dry state before use, and its moisture content is preferably less than or equal to 10.0 wt. %, further preferably less than or equal to 5.0 wt. %, more preferably less than or equal to 1.0 wt. %, based on the total weight of the adhesive coating.

The acrylated biodegradable polymer, for example, one or a mixture of any two or more of acrylated gelatin, acrylated hyaluronic acid, acrylated chitosan, acrylated alginic acid, and poly(ethylene glycol) diacrylate, has preferably a degree of substitution of acrylyl of 10% to 80%. In some embodiments of the present disclosure, the acrylated biodegradable polymer is acrylated gelatin having a degree of substitution of acrylyl of 10% to 80%. In some embodiments of the present disclosure, the acrylated biodegradable polymer is acrylated hyaluronic acid having a degree of substitution of acrylyl of 10% to 80%. In some embodiments of the present disclosure, the acrylated biodegradable polymer is acrylated chitosan having a degree of substitution of acrylyl of 10% to 80%.

A crosslinking agent known in the art may be used to form the crosslinked copolymer, including, but not limited to, α-ketoglutaric acid, ammonium persulfate, hydrogen peroxide, and AIBN. In one embodiment of the present disclosure, the crosslinking agent is α-ketoglutaric acid.

The additional biodegradable polymer includes, but is not limited to, gelatin, chitosan, collagen, hyaluronic acid, alginic acid or salts thereof, polyethylene glycol, and polyvinyl alcohol. In some embodiments of the present disclosure, the biodegradable polymer is selected from the group consisting of gelatin, chitosan, collagen, hyaluronic acid, and alginate. In one embodiment of the present disclosure, the biodegradable polymer is gelatin.

The present disclosure further provides a method of preparing the self-adhesive absorbable biological patch.

According to the present disclosure, the method comprises preparing an adhesive coating, and coating the coating on a substrate layer.

According to the present disclosure, the preparation method of the adhesive coating comprises mixing respective components to prepare a precursor solution mixture of the adhesive coating, and the precursor solution mixture comprises, based on the total mass of the mixture, 5.0 to 30.0 wt. % of acrylic acid and/or acrylamide, 0.2 to 5.0 wt. % of acrylated biodegradable polymer, 0.1 to 5.0 wt. % of acrylic acid-N-succinimidyl ester, 0 to 15.0 wt. % of additional biodegradable polymer, and a crosslinking amount of crosslinking agent. The solvent system of the precursor solution mixture is an aqueous solution.

According to the present disclosure, when the mass percentage of acrylic acid and/or acrylamide in the precursor solution mixture is between 5.0 and 30.0 wt. %, the formed self-adhesive absorbable biological patch is allowed to have both good tissue adhesiveness and compliance. The mass percentage of acrylic acid and/or acrylamide in the precursor solution mixture is preferably 10.0 to 30.0 wt. %, more preferably 20.0 to 30.0 wt. %.

According to the present disclosure, when the mass percentage of the acrylated biodegradable polymer in the precursor solution mixture is between 0.2 and 5 wt. %, the formed self-adhesive absorbable biological patch is allowed to have good tissue adhesiveness, mechanical strength, and compliance at the same time. The mass percentage of the acrylated biodegradable polymer in the precursor solution mixture is preferably 0.5 to 4.0 wt. %, more preferably 1.0 to 3.0 wt. %.

According to the present disclosure, when the mass percentage of acrylic acid-N-succinimidyl ester in the precursor solution mixture is between 0.1 and 5.0 wt. %, the formed self-adhesive absorbable biological patch is allowed to have good tissue adhesiveness. The mass percentage of the acrylic acid-N-succinimidyl ester in the precursor solution mixture is preferably 0.5 to 3.0 wt. %, more preferably 0.8 to 1.2 wt. %.

According to the present disclosure, the biodegradable polymer may further improve the hydration ability and mechanical strength of hydrogel, thereby improving its tissue compliance. Besides, the biodegradable polymer can also regulate the biodegradation rate of the adhesive coating, and its mass percentage in the precursor solution mixture is between 0 and 15.0 wt. %. The mass percentage of the biodegradable polymer in the precursor solution mixture is preferably 5 to 15 wt. %, for example, it may be more preferably 8 to 12.0 wt. %.

According to the present disclosure, the mass percentage of the crosslinking agent in the precursor solution mixture is preferably 0.1 to 0.3 wt. %.

In a preferred embodiment of the present disclosure, the precursor solution mixture comprises 20.0 to 30.0 wt. % of acrylic acid and/or acrylamide, 1.0 to 3.0 wt. % of acrylated biodegradable polymer, 0.8 to 1.2 wt. % of acrylic acid-N-succinimidyl ester, 5 to 15% of biodegradable polymer, and 0.1 to 0.3 wt. % of crosslinking agent.

According to the present disclosure, when the precursor solution mixture is coated directly on the substrate layer to form an adhesive coating, the coating may use a coating method known in the art, and may be manual coating or machine coating. According to the present disclosure, the coating amount of the precursor solution mixture of the adhesive coating is 10 to 300 $\mu L/cm^2$.

According to the present disclosure, the preparation method further comprises a step of subjecting the adhesive coating to crosslinking treatment (e.g., light or heat treatment), so as to have the adhesive coating fully polymerized and crosslinked. It is preferable to perform the crosslinking with ultraviolet light (10 to 400 nm, e.g., 354 nm, 360 nm or 365 nm), and the illumination time for crosslinking depends on the amount of the adhesive coating and may typically be 5 min to 48 h, for example, 20 min to 12 h, more preferably 3 to 5 h.

According to the present disclosure, the method further comprises subjecting the adhesive coating to dialysis treatment to remove water-soluble monomers such as acrylic acid and improve the biocompatibility of the finally prepared self-adhesive absorbable biological patch. It is preferable to perform the dialysis with water, and the temperature may be 15° C. to 35° C. In order to improve the dialysis efficiency, stirring or shaking may be carried out simultaneously. The dialysis treatment is performed after the crosslinking treatment.

According to the present disclosure, the step of coating the adhesive coating on the substrate layer and the steps of subjecting the adhesive coating to crosslinking treatment and dialysis treatment may be reversed in order. The precursor solution mixture may be coated on the substrate layer and then crosslinked and dialyzed, or the precursor solution mixture may be crosslinked and dialyzed and then coated on the substrate layer, or the precursor solution mixture is crosslinked, coated on the substrate layer, and then dialyzed.

In one embodiment of the present disclosure, the precursor solution mixture of the adhesive coating is coated on the substrate layer, and then subjected to crosslinking treatment with ultraviolet light and to dialysis treatment after the crosslinking is completed.

According to the present disclosure, the preparation method further comprises subjecting the self-adhesive absorbable biological patch to dehydration treatment to contribute to storage and transportation. The dehydration treatment may be a dehydration method known in the art, including, but not limited to, freeze-drying, vacuum drying, and heat drying. In one embodiment of the present disclosure, freeze-drying is used.

In some embodiments of the present disclosure, the precursor solution mixture of the adhesive coating is coated on the substrate layer in a coating amount of 10 to 300 $\mu L/cm^2$. After being infiltrated with the precursor solution mixture, the substrate layer is illuminated with ultraviolet light for 3 to 5 h to form a self-adhesive absorbable biological patch.

After being dialyzed and soaked in deionized water for 3 to 7 days, the biological patch is freeze-dried for 3 to 7 days to obtain a self-adhesive absorbable biological patch in a dry gel.

The present disclosure further provides a kit, comprising a substrate layer and an adhesive coating, which are individually packaged, respectively.

According to the present disclosure, the substrate layer and the adhesive coating are as described above, respectively. Preferably, both the substrate layer and the adhesive coating in individual packages are in a dry state.

When in use, the substrate layer and the adhesive coating are taken out from their respective packages. The surface of the substrate layer in contact with the adhesive coating is wetted with an aqueous solution. The adhesive coating is coated on the substrate layer. Afterwards, the free surface of the adhesive coating is brought into contact with the tissue surface to be sealed.

In a dry state (i.e., a dry gel state), the adhesive coating may serve as a self-adhesive absorbable planar film. Therefore, the second aspect of the present disclosure provides a dry adhesive material for bonding a tissue surface.

According to the present disclosure, the dry adhesive material is in the form of a film, sheet or strip having a top surface and a bottom surface. When cut into a suitable size, it can be used as the adhesive coating described above in the present disclosure to form the self-adhesive absorbable biological patch of the present disclosure together with the material for the substrate layer.

Having the same composition of the above-mentioned adhesive coating, the dry adhesive material comprises a succinimidyl ester group-grafted polyacrylic crosslinked copolymer, and further optionally contains a biodegradable polymer.

The polyacrylic crosslinked copolymer preferably has a molecular weight of 10 kDa to 1000 kDa. The crosslinked copolymer can absorb water in an aqueous environment to form a gel, and is formed by polymerizing and crosslinking acrylic acid and/or acrylamide with an acrylated biodegradable polymer and acrylic acid-N-succinimidyl ester.

According to the present disclosure, in the succinimidyl ester group-grafted polyacrylic crosslinked copolymer, the weight ratio of acrylic acid and/or acrylamide, the acrylated biodegradable polymer, and acrylic acid-N-succinimidyl ester as three monomers is (50 to 300):(2 to 50):(1 to 50), preferably (200 to 300):(2 to 30):(1 to 20), more preferably (200 to 300):(2 to 10):(1 to 10).

According to the present disclosure, in the dry adhesive material, the amount of the succinimidyl ester group-grafted polyacrylic crosslinked copolymer is 4 to 120 $mg/cm^2$, preferably 10 to 80 $mg/cm^2$, more preferably 20 to 40 $mg/cm^2$; and the amount of the biodegradable polymer is 0 to 30 $mg/cm^2$, preferably 1 to 20 $mg/cm^2$, more preferably 5 to 10 $mg/cm^2$.

According to the present disclosure, in the dry adhesive material, the weight ratio of the succinimidyl ester group-grafted polyacrylic crosslinked copolymer to the biodegradable polymer is (1 to 8):(0 to 3), preferably (2 to 8):(1 to 3), more preferably (2.7 to 4.3):(1 to 1.5).

The dry adhesive material may be loaded with an additional active material including, but not limited to, protein drugs, polypeptides, growth factors, enzymes and the like, or antibacterial or anti-inflammatory drugs, cationic surfactants, polyphenols and the like, or metals and compounds thereof such as magnesium oxide, calcium carbonate and the like. The active material endows the dry adhesive material with various biological functions and uses. The active material may be present in the dry adhesive material by physically mixing, or may be present in the dry adhesive material by chemically covalently bonding.

According to the present disclosure, the moisture content of the dry adhesive material is less than or equal to 10.0 wt. %, further preferably less than or equal to 5.0 wt. %, more preferably less than or equal to 1.0 wt. %, based on the total weight of the dry adhesive material.

The acrylated biodegradable polymer, for example, one or a mixture of any two or more of acrylated gelatin, acrylated hyaluronic acid, acrylated chitosan, acrylated alginic acid, and poly(ethylene glycol) diacrylate, has preferably a degree of substitution of acrylyl of 10% to 80%. In some embodiments of the present disclosure, the acrylated biodegradable polymer is acrylated gelatin having a degree of substitution of acrylyl of 10% to 80%. In some embodiments of the present disclosure, the acrylated biodegradable polymer is acrylated hyaluronic acid having a degree of substitution of acrylyl of 10% to 80%. In some embodiments of the present disclosure, the acrylated biodegradable polymer is acrylated chitosan having a degree of substitution of acrylyl of 10% to 80%.

A crosslinking agent known in the art may be used to form the crosslinked copolymer, including, but not limited to, $\alpha$-ketoglutaric acid, ammonium persulfate, hydrogen peroxide, AIBN and the like. In one embodiment of the present disclosure, the crosslinking agent is $\alpha$-ketoglutaric acid.

The biodegradable polymer includes, but is not limited to, gelatin, chitosan, collagen, hyaluronic acid, alginic acid or salts thereof, polyethylene glycol, polyvinyl alcohol and the like. In some embodiments of the present disclosure, the biodegradable polymer is selected from the group consisting of gelatin, chitosan, collagen, hyaluronic acid, and alginate. In one embodiment of the present disclosure, the biodegradable polymer is gelatin.

The present disclosure further provides a precursor solution mixture for forming the dry adhesive material or adhesive coating.

The precursor solution mixture comprises, based on the total mass of the mixture, 5.0 to 30.0 wt. % of acrylic acid and/or acrylamide, 0.2 to 5.0 wt. % of acrylated biodegradable polymer, 0.1 to 5.0 wt. % of acrylic acid-N-succinimidyl ester, 0 to 15.0 wt. % of biodegradable polymer, and a crosslinking amount of crosslinking agent.

In the precursor solution mixture, the mass percentage of acrylic acid and/or acrylamide is preferably 10.0 to 30.0 wt. %, more preferably 20.0 to 30.0 wt. %.

In the precursor solution mixture, the mass percentage of the acrylated biodegradable polymer is preferably 0.5 to 4.0 wt. %, more preferably 1.0 to 3.0 wt. %.

In the precursor solution mixture, the mass percentage of acrylic acid-N-succinimidyl ester is preferably 0.5 to 3.0 wt. %, more preferably 0.8 to 1.2 wt. %.

In the precursor solution mixture, the mass percentage of the biodegradable polymer is preferably 5 to 15 wt. %, for example, it may be more preferably 8 to 12.0 wt. %.

Preferably, the content of the crosslinking agent in the precursor solution mixture is 0.1 to 0.3 wt. %.

In one embodiment of the present disclosure, the precursor solution mixture comprises 20.0 to 30.0 wt. % of acrylic acid and/or acrylamide, 1.0 to 3.0 wt. % of acrylated biodegradable polymer, 0.8 to 1.2 wt. % of acrylic acid-N-succinimidyl ester, 5.0 to 15.0 wt. % of biodegradable polymer, and 0.1 to 0.3 wt. % of $\alpha$-ketoglutaric acid.

The third aspect of the present disclosure provides a kit, comprising an individually packaged substrate layer, and an individually packaged precursor solution mixture for forming an adhesive coating. The precursor solution mixture is as described previously.

When in use, the substrate layer and the precursor solution mixture are taken out from the packages, and prepared into a usable patch by the preparation method of a self-adhesive absorbable biological patch described above in the present disclosure.

The fourth aspect of the present disclosure provides a therapeutic agent delivery device for sealing a tissue surface and releasing one or more therapeutic agents to a target site, the device comprising: (i) a self-adhesive absorbable biological patch, and (ii) a plaster loaded with one or more therapeutic agents, wherein the area of the plaster is smaller than the area of the self-adhesive absorbable biological patch, and the plaster is located on a free surface of an adhesive coating of the self-adhesive absorbable biological patch. The self-adhesive absorbable biological patch is as described previously in the present disclosure.

The fifth aspect of the present disclosure provides use of the self-adhesive absorbable biological patch, the dry adhesive material or the precursor solution mixture in the preparation of a tissue sealing material.

The present disclosure further provides a method of sealing a tissue wound or wound surface, wherein the method is to apply a self-adhesive absorbable biological patch according to the present disclosure to a tissue wound or wound surface in need of being sealed, adhering a free surface of an adhesive coating of the biological patch to the tissue wound or wound surface in need of being sealed.

The present disclosure further provides a method of releasing one or more therapeutic agents to a target site, comprising: providing a therapeutic agent delivery device as described above in the present disclosure, and bringing a free surface of an adhesive coating of the self-adhesive absorbable biological patch into contact with a tissue surface.

The surface of the tissue to be sealed in the present disclosure may be dry or wet. For a dry tissue surface, the surface may be wetted with an aqueous solution prior to the application of the self-adhesive absorbable biological patch. For a wet tissue surface, the self-adhesive absorbable biological patch may be directly applied thereon or the surface may be further wetted with an aqueous solution prior to the application of the self-adhesive absorbable biological patch.

In the present disclosure, an "aqueous solution" is a solution with water as a solvent system, and has a pH of preferably 6.9 to 7.5, most preferably 7.0 to 7.4, which includes, but is not limited to, water, normal saline, physiologically acceptable buffer solution (such as a PBS solution) and the like.

The present application combines a polyacrylic crosslinked copolymer with succinimidyl ester and a biodegradable polymer to form an adhesive hydrogel on a substrate layer and subjects the adhesive hydrogel to freeze-drying treatment to form a self-adhesive absorbable biological patch. In the adhesive coating, the crosslinked copolymer of polyacrylic acids is the main structure of the adhesive hydrogel, and free carboxyl groups in the crosslinked copolymer form an electrostatic force with free groups on the body tissue surface to generate an adhesive effect. The adherence is reversible, and the biological patch can be torn off after adhering to the tissue surface and still has the adhesive effect when repositioned and adhered to a tissue surface. Succinimidyl esters distributed in the hydrogel form an amide bond with the free amino groups on the body tissue surface to improve the adhesive strength between the tissue and the patch. Since the amide bond is a chemical covalent bond, the adhesive strength thereby formed is greater than that formed by the electrostatic force, thereby ensuring the high adhesive strength of the patch on the tissue surface and achieving stable sealing of the wound surface. The biodegradable polymers distributed in the hydrogel form a composite structure together with the hydrogel structure. After the hydrogel structure is implanted in the body, the biodegradable polymers will be the first to decompose, and the resulting voids increase the specific surface area of the hydrogel in contact with water, which is beneficial to ensure the degradation of the hydrogel in the body. Moreover, neither the electrostatic force nor the amide bond is affected by the tissue fluid environment, so this self-adhesive patch can still maintain a high viscosity in the tissue fluid environment.

The present inventors have found in their studies that if the concentration of acrylic acid and/or acrylamide in the precursor solution mixture of the adhesive coating is different, the tissue adhesiveness of the finally resulting hydrogel is also different, that is, the tissue adhesiveness increases with the increase in the concentration of acrylic acid and/or acrylamide. However, hydrogels formed by acrylic acids and/or acrylamides at different concentrations have different elastic modulus, which basically follows the rule that the elastic modulus of the hydrogel increases with the increase in the concentration of acrylic acid and/or acrylamide. Nevertheless, an excessively high elastic modulus does not match the mechanical strength of the tissue in the body, and the tissue compliance is poor. In order for the adhesive coating to have both sufficiently high tissue adhesiveness and an appropriate elastic modulus, the inventors have conducted extensive researches and found the appropriate amounts of acrylic acid and/or acrylamide, the acrylated biodegradable polymer, and acrylic acid-N-succinimidyl ester as three kinds of monomers, and the appropriate amount of the biodegradable polymer to cooperate with them.

The chemical composition of the adhesive coating is selected such that in addition to good adhesiveness, the adhesive coating also has suitable mechanical properties that are matched and harmonized with those of the substrate layer. One of the self-adhesive absorbable biological patches prepared in the present disclosure is taken as an example.

| Mechanical Parameter | SIS | SIS/Adhesive Coating |
|---|---|---|
| Elastic modulus (MPa) | 79.9 | 84.4 |
| Tensile strength (MPa) | 7.1 | 6.4 |
| Maximum deformation (%) | 3.3 | 4.7 |

As shown above, the mechanical strength of the biological patch with the adhesive coating of the present disclosure is mainly provided by the SIS substrate layer, and the adhesive coating does not have an excessive impact on the mechanical properties of the substrate layer, so that the biological patch as a whole has similar tissue compliance to that of SIS.

The self-adhesive absorbable biological patch of the present disclosure has a degree of flexibility and can withstand the tensile strain within 6% of itself, and its Young's modulus can be as high as 93.36 MPa, which satisfy the dynamic mechanical microenvironment in vivo, so that the biological patch can adhere tightly to the tissue surface, and even if the tissue is deformed due to the pulsation or twisting, the biological patch can still maintain the tight adherence. Through the shear tensile and peeling experiments, it is calculated that the adhesive strength of the self-adhesive absorbable biological patch of the present disclosure can reach a level higher than the normal pulmonary physiological pressure (2.7 kPa) or arterial pressure (10 to 16 kPa) of human body, and its shear adhesive strength and interfacial toughness can even reach 39.4 kPa and 288.9 $J \cdot m^{-2}$, respectively. Therefore, the self-adhesive absorbable biological patch of the present disclosure can be used for tissue sealing including arterial hemostasis and lung air leakage sealing.

Additionally, when acrylic acid and/or acrylamide are coated together with the acrylated biodegradable polymer, acrylic acid-N-succinimidyl ester, and the biodegradable polymer on the substrate layer and treated to form an adhesive coating, the surface of the adhesive coating in contact with the substrate layer may be chemically bonded first, that is, the chemical groups such as a carboxyl group and a succinimidyl ester group in the adhesive hydrogel and the chemical groups such as an amino group in the substrate layer undergo an esterification or amidation reaction. After the self-adhesive patch is freeze-dried, the surface of the adhesive coating (in a dry gel state) in contact with the substrate layer may be considered no longer to have the tissue adhesiveness, while the exposed surface assumes the role of tissue adherence and sealing. Such a way of their combination can circumvent tissue adhesion caused by possibly non-selective adherence of the exposed surface to other surrounding tissues when the adhesive coating in dry gel state is used alone to adhere tissues.

The performance comparisons between the self-adhesive absorbable biological patch of the present disclosure and other commercialized tissue adhesives are listed in the tables below.

TABLE 1

Comparison of tissue adhesive strength between self-adhesive absorbable biological patch and commercialized tissue adhesive materials

| Name | Tissue Adhesive Strength (kPa) |
|---|---|
| Self-adhesive absorbable biological patch | ~39.4 |
| TissuePatch | ~20 |
| Hemopatch | ~1 |

TABLE 2

Comparison of cytocompatibility between self-adhesive absorbable biological patch and commercialized tissue adhesive materials

| Name | Cell Activity (%) |
|---|---|
| Self-adhesive absorbable biological patch | ~90 |
| α-Cyanoacrylate | ~50 |
| BioGlue | ~60 |

TABLE 3

Comparison of biodegradability between self-adhesive
absorbable biological patch and commercialized
tissue adhesive materials

| Name | Degradation Cycle (Day) |
|---|---|
| Self-adhesive absorbable biological patch | 30 to 90 |
| TissuePatch | ~40 |
| Hemopatch | ~30 |
| α-Cyanoacrylate | Non-degradable |
| BioGlue | Non-degradable |

Therapeutic use of the self-adhesive absorbable biological patch of the present disclosure The biological patch of the present disclosure is applicable to both the internal surfaces and external surfaces of the body, that is, it may be applied topically to the exterior of the body (e.g., applied to the skin), or applied topically to the internal surfaces, such as surfaces of internal organs exposed during operation or trauma, and the operation includes both conventional operations and minimally invasive operations.

The biological patches of the present disclosure are particularly suitable for the internal surfaces of the body.

The biological patches of the present disclosure are particularly suitable for operative applications in the following areas: thoracic/cardiovascular, otolaryngology, urinary system, oral/maxillofacial, plastic surgery, nervous system, gastrointestinal system, ophthalmology, gynecology/obstetrics. Exemplary uses are as follows:

Skin Closure

Biological patches may be applied topically to promote wound closure (as an alternative to sutures), which can reduce scars. Therefore, in minor operations (e.g., in accidents and first-aids), the self-adhesiveness of the biological patches, if used, allows for ease of their rapid application.

Wound Healing

The degradability of the biological patch means that it can support and promote wound healing. Once the biological patch starts to degrade, fibroblasts will migrate into the extracellular matrix and deposit therein. Therefore, the biological patch may be used as a dressing for the internal or external surface. Besides, factors known to promote skin cell proliferation, such as growth factors and cAMP, may be added to the biological patch to promote healing. An anti-infective drug or the like may also be added to the biological patch to make it particularly useful for treating burns.

Hernia Repair

In herniorrhaphy, biological patches may be used to provide reinforcement. The self-adhesive connection overcomes the potential problems faced with conventional surgical reinforcement patch products, such as the need to cooperate with suturing or stapling. Biological patches for use in herniorrhaphy may be designed to have short-term or long-term durability depending on the requirements for tissue repair. Of course, the biological patches of the present disclosure can withstand stapling.

Anastomosis

Self-adhesive patches provide a means to quickly seal and connect tubular structures such as blood vessels, vascular grafts, bladder grafts, and gastrointestinal tracts, and prevent them from leaking.

Large Tissue Area Sealing

Good sealing and handling properties of the biological patch, together with its self-adhesiveness and ability to cover a large surface area, mean that it is particularly useful for sealing excised tissue surfaces, especially those (e.g., liver, spleen, and kidney) where diffuse bleeding occurs. The biological patch may also provide a desirable support matrix for tissue repair at these locations. The biological patch may also be used to limit the leakage of cerebrospinal fluid after neurosurgery.

Air Leakage Sealing

The high tensile strength and good inherent elasticity of the biological patch (after hydration and reaction with active functional groups of the tissue) make it particularly suitable for sealing air leakage in the lung, especially after pneumonectomy. Moreover, after sealing, the biological patch provides a desirable support matrix for tissue repair at these locations.

Hemostasis

The biological patch may be applied to a bleeding area as a physical barrier. Tissue active materials in the biological patch may immobilize proteins to thereby promote hemostasis.

Administration of Therapeutic Agents

Drugs and other therapeutic agents (including biologically active agents such as growth factors, and even cells and cellular components) may be added to the solution used for forming the adhesive coating component, or covalently bonded to the component before the component is used to manufacture a biological patch.

Postoperative Adhesion Prevention

Postoperative adhesion is formation of disordered connective tissues between adjacent tissues, which is prone to serious postoperative complications. For example, in intestinal operations, the postoperative adhesion may cause intestinal entanglement, which leads to a further operation. Applying the biological patch with self-adhesiveness in the present disclosure to the tissue exposed during operation can effectively prevent postoperative adhesion between this tissue and adjacent tissues.

Minimally Invasive Operation

The adoption of minimally invasive techniques to collect tissue samples through biopsy, insert instruments, deliver therapeutic agents, and implement operative approaches has become an alternative to conventional "open" operations. The biological patch is shaped or manufactured into an appropriate size and configuration, and introduced into the body through a specially designed available minimally invasive operative instrument and trocar system, and its self-adhesiveness is utilized to significantly reduce the technical difficulties related to manipulation, closure, and repair of tissues.

The biological materials as the substrate layer are all biological materials known in the art, or may be prepared by the methods known in the art.

For example, SIS, dermis, and pericardium are all known in the art. It is also known in the art to decellularize them to obtain decellularized extracellular matrices of the corresponding tissues. Decellularized SIS, decellularized dermis, and decellularized pericardium have been commercially available, or may also be prepared by methods known in the art.

For example, in some embodiments of the present disclosure, SIS or dermis or pericardium is treated with ultrasound to obtain decellularized SIS, decellularized dermis or decellularized pericardium. In one embodiment of the present disclosure, the frequency of the ultrasonic treatment is 20 to 80 KHz. In another embodiment of the present disclosure, the ultrasonic treatment is multi-frequency ultrasonic treatment, and the low-frequency ultrasonic treatment is used before the high-frequency ultrasonic treatment. Preferably, the low-frequency range is from 20 to 40 KHz, and the high-frequency range is from 60 to 90 KHz, where the low-frequency treatment is carried out for 5 to 40 min, and the high-frequency treatment is carried out for 5 to 40 min.

In some embodiments of the present disclosure, the SIS or dermis or pericardium is treated with a solution containing trypsin and EDTA or a salt thereof to obtain decellularized SIS, decellularized dermis or decellularized pericardium. Preferably, the concentration of trypsin in the solution is 0.01 to 0.2% by mass, preferably 0.02 to 0.05% by mass, and the concentration of EDTA or a salt thereof (such as EDTA-2Na or EDTA-4Na) is 0.1 to 1 mmol/L, preferably 0.4 to 0.8 mmol/L; the pH value of the solution is 7.0 to 8.0, preferably 7.2 to 7.5.

In some embodiments of the present disclosure, multi-frequency ultrasound and a solution containing trypsin and EDTA or a salt thereof are used in combination to treat the SIS or dermis or pericardium to obtain decellularized SIS, decellularized dermis or decellularized pericardium.

In some embodiments of the present disclosure, decellularized SIS, decellularized dermis, decellularized pericardium or the like may be prepared by the preparation methods disclosed in Chinese Patent No. CN103272278B or CN107007886B, the entire contents of which are incorporated herein.

The collagen used in the present disclosure may be derived from any collagen suitable for gel formation, including substances from liquid, slurry, fibrous or powdery collagen materials that can be processed into porous or fibrous matrices. To improve the gel-forming ability or solubility, the collagen may be (partially) hydrolyzed or modified as long as a stable substrate layer is formed when drying.

Natural gelatin is inexpensive and available in large quantities, and can be gained from many sources. Gelatin is a hydrolysate of collagen. Convenient animal sources of gelatin and collagen include chicken, turkey, cattle, pig, horse or human sources. Collagen may also be artificial collagen or recombinant collagen. Preferably, the gelatin is crosslinked to prevent complete dissolution. Crosslinking can be achieved by incomplete hydrolysis of collagen or by chemical crosslinking using a crosslinking agent such as formaldehyde or divalent aldehyde.

Definitions of Terms

Unless otherwise defined, all technical and scientific terms used herein have the same meanings as commonly understood by one of ordinary skill in the art. In case of any contradiction, the definitions provided in the present application shall prevail. Trade name, when used herein, is intended to refer to its corresponding merchandise or its active ingredient. Patents, published patent applications, and publications cited herein are all incorporated herein by reference.

The term "comprising", "including", "having", "containing" or "involving" and other variants thereof used herein are intended to be inclusive or open-ended, and does not exclude other unrecited elements or methods and steps. It should be appreciated to a person skilled in the art that the above term such as "comprising" encompasses the meaning of "consisting of . . . ".

The terms "selected from the group consisting of . . . ", "preferably . . . ", and "more preferably . . . " refer to independent selection from one or more elements in the group listed thereafter, and may include a combination of two or more elements. In the present disclosure, one of the elements in the group listed thereafter is preferred.

The term "optional", "optionally", or "optionally present" means that the event or situation described subsequently may, but does not necessarily, occur, and the description includes the case where the event or situation occurs and the case where the event or situation does not occur.

In the present disclosure, the term "may" is used to indicate two meanings of performing and not performing certain processing.

In the present disclosure, the numerical range represented by "numerical value A to numerical value B" is used to indicate the range including the endpoint values A and B.

In the present disclosure, "water" includes any usable water such as deionized water, distilled water, ion exchange water, double distilled water, high purity water, and pure water.

In the present disclosure, the free surface of the adhesive coating refers to the surface of the adhesive coating in contact with the tissue, which is opposite to the contact surface between the adhesive coating and the substrate layer.

DETAILED DESCRIPTION

Figure 1:
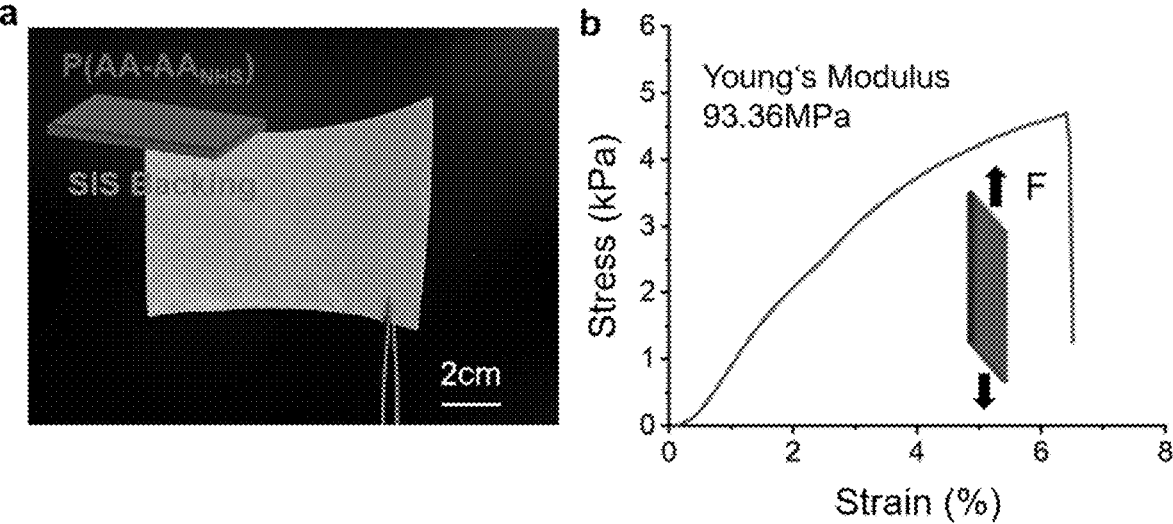
FIG. 1 (a) is the appearance of a self-adhesive absorbable biological patch: a decellularized extracellular matrix of porcine small intestinal submucosa (SIS) is used as a substrate layer, and a gel coating of a succinimidyl ester-grafted polyacrylic crosslinked copolymer is coated on the surface of the substrate layer, and freeze-dried to show the appearance; (b) is a stress-strain curve of a self-adhesive absorbable biological patch, showing that the biological patch can withstand the tensile strain within 6% of itself and has a Young's modulus of up to 93.36 MPa.

The technical solution of the present disclosure will be further explained in detail below with reference to specific examples. It should be appreciated that the following examples are only intended to schematically illustrate and explain the present disclosure and shall not be construed as limitations on the scope of protection for the present disclosure. Any technology implemented based on the above contents of the present disclosure is covered in the scope sought to be protected by the present disclosure.

Unless otherwise stated, the raw materials and reagents used in the examples below are all commercially available or may be prepared by known methods.

Example 1: Preparation of Self-Adhesive Absorbable Biological Patch

Raw materials were dissolved in deionized water at 37° C. to form a homogeneous aqueous solution containing 30.0 wt. % of acrylic acid (analytical reagent, Aladdin), 1.0 wt. % of acrylic acid-N-succinimidyl ester (analytical reagent, Aladdin), 10.0 wt. % of gelatin (pigskin-derived, Sigma-Aldrich), 2.0 wt. % of acrylated gelatin (50% degree of substitution for acrylization, as measured by formaldehyde titration), and 0.2 wt. % of α-ketoglutaric acid (Sigma-Aldrich), thereby obtaining a precursor solution mixture of an adhesive coating.

Decellularized porcine small intestinal submucosa (SIS) (the product of Beijing Biosis Healing Biological Technology Co., Ltd., 0.17 mm thick, composed of 4 layers of decellularized small intestinal submucosa) was taken as a substrate layer. The precursor solution mixture of the adhesive coating was coated uniformly on the substrate layer in a coating amount of 80 μL/cm$^2$. After being infiltrated with the precursor solution mixture, the substrate layer was continuously illuminated with ultraviolet light (360 nm) for 3 h, then dialyzed for 3 days, and freeze-dried to form a self-adhesive absorbable biological patch.

Example 2: Preparation of Self-Adhesive Absorbable Biological Patch

Raw materials were dissolved in normal saline to form a homogeneous aqueous solution containing 5.0 wt. % of acrylic acid, 0.1 wt. % of acrylic acid-N-succinimidyl ester, 15.0 wt. % of hyaluronic acid (Bloomage Freda Biopharm Co., Ltd.), 5.0 wt. % of acrylated hyaluronic acid (50% degree of substitution for acrylization, as measured by formaldehyde titration), and 0.2 wt. % of α-ketoglutaric acid, thereby obtaining a precursor solution mixture of an adhesive coating.

SIS (the product of Beijing Biosis Healing Biological Technology Co., Ltd., 0.17 mm thick, composed of 4 layers of decellularized small intestinal submucosa) was taken as a substrate layer. The precursor solution mixture of the adhesive coating was evenly coated on the substrate layer in a coating amount of 100 μL/cm$^2$. After being infiltrated with the precursor solution mixture, the substrate layer was continuously illuminated with ultraviolet light (360 nm) for 12 h, then dialyzed for 5 days, and freeze-dried to form a self-adhesive absorbable biological patch.

Example 3: Preparation of Self-Adhesive Absorbable Biological Patch

Raw materials were dissolved in normal saline to form a homogeneous aqueous solution containing 10.0 wt. % of acrylic acid, 3.0 wt. % of acrylic acid-N-succinimidyl ester, 5.0 wt. % of chitosan (Aldrich), 1.0 wt. % of acrylated chitosan (50% degree of substitution for acrylization, as measured by formaldehyde titration), and 0.2 wt. % of ammonium persulfate (Sigma-Aldrich), thereby obtaining a precursor solution mixture of an adhesive coating.

A collagen membrane (prepared from a collagen solution by freeze-drying, 0.3 mm thick) was taken as a substrate layer. The precursor solution mixture of the adhesive coating was coated uniformly on the substrate layer in a coating amount of 300 μL/cm$^2$. After being infiltrated with the precursor solution mixture, the substrate layer was continuously illuminated with ultraviolet light (360 nm) for 3 h, then dialyzed for 5 days, and freeze-dried to form a self-adhesive absorbable biological patch.

Example 4: Preparation of Dry Adhesive Material

Raw materials were dissolved in deionized water at 37° C. to form a homogeneous aqueous solution containing 20.0 wt. % of acrylic acid, 5.0 wt. % of acrylic acid-N-succinimidyl ester, 5.0 wt. % of gelatin, 1.0 wt. % of acrylated gelatin (50% degree of substitution for acrylization), and 0.2 wt. % of α-ketoglutaric acid, thereby obtaining a precursor solution mixture of an adhesive coating.

The precursor solution mixture of the adhesive coating was coated uniformly on a polytetrafluoroethylene film in a coating amount of 10 μL/cm$^2$. The film was continuously illuminated with ultraviolet light (360 nm) for 5 h, then dialyzed for 3 days, and freeze-dried to form a dry adhesive material.

Example 5: Preparation of Self-Adhesive Absorbable Biological Patch

Raw materials were dissolved in deionized water at 37° ° C. to form a homogeneous aqueous solution containing 30.0 wt. % of acrylic acid, 1.0 wt. % of acrylic acid-N-succinimidyl ester, 10.0 wt. % of gelatin, 1.0 wt. % of acrylated gelatin (50% degree of substitution for acrylization), 0.2 wt. % of α-ketoglutaric acid, and 0.1 wt. % of benzalkonium chloride, thereby obtaining a precursor solution mixture of an adhesive coating.

SIS (the product of Beijing Biosis Healing Biological Technology Co., Ltd., 0.17 mm thick, composed of 4 layers of decellularized small intestinal submucosa) was taken as a substrate layer. The precursor solution mixture of the adhesive coating was coated uniformly on the substrate layer in a coating amount of 50 μL/cm$^2$. After being infiltrated with the precursor solution mixture, the substrate layer was continuously illuminated with ultraviolet light (360 nm) for 200 min, then dialyzed for 3 days, and freeze-dried to form a self-adhesive absorbable biological patch. This self-adhesive absorbable biological patch had certain antibacterial and disinfection characteristics due to the addition of benzalkonium chloride.

Experimental Example 1: Stress-Strain Experiment

The self-adhesive absorbable biological patch obtained in Example 1 was used as an experimental sample, cut into a size of 2 cm×5 cm, and installed in a universal tensile testing machine. Parameters were set as follows: the sample was stretched at the effective length of 2 cm, the width of 2 cm, the thickness of 0.17 mm, and the tensile speed of 10 mm/min at room temperature. The Young's modulus was the slope of the stress-strain curve in the elastic deformation interval. The results were as shown in FIG. 1($b$).

Experimental Example 2: Enzymolysis Experiment

Figure 2:
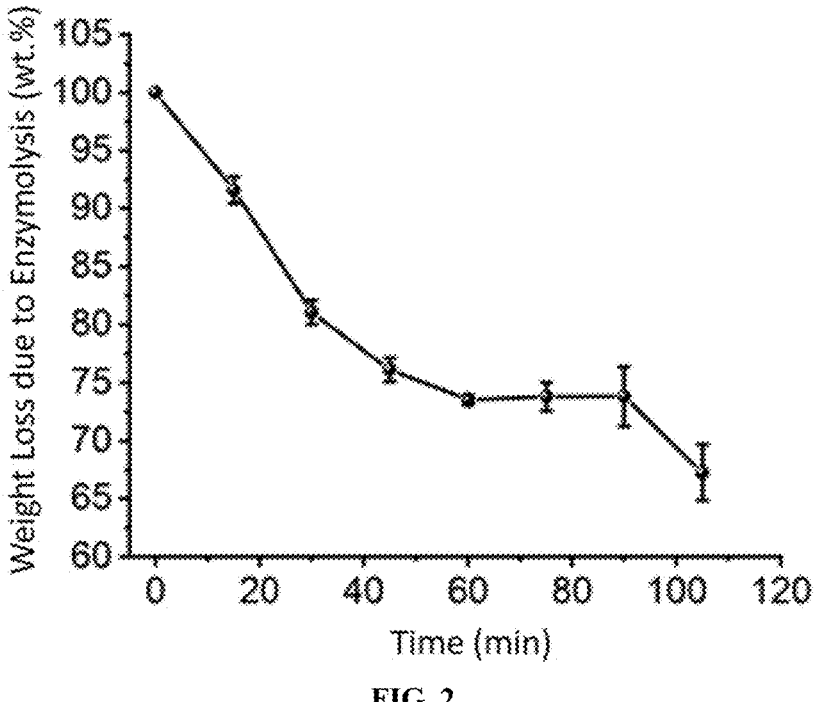
FIG. 2 shows a statistic diagram for in vitro enzymolysis of a self-adhesive absorbable biological patch. The material is soaked in an aqueous proteinase K solution and its mass gradually decreases with time, indicating that the material has biodegradability.

The self-adhesive absorbable biological patch obtained in Example 1 was used as an experimental sample. The 2 cm×5 cm self-adhesive absorbable biological patch was weighed, and the initial mass was recorded as $W_0$. Thereafter, the biological patch was soaked in 30 mL of 1 mg/20 mL proteinase K solution, and incubated in a water bath shaker at 37° ° C. and 60 rpm. The patch was taken out every 15 min, gently rinsed with deionized water three times, and then freeze-dried and weighed. The mass was recorded as $W_t$. Weight loss due to enzymolysis $(W_1\%)=(1-W_t/W_0)\times 100\%$. The results were as shown in FIG. 2.

Experimental Example 3: Shear Adhesive Strength Test

Figure 3:
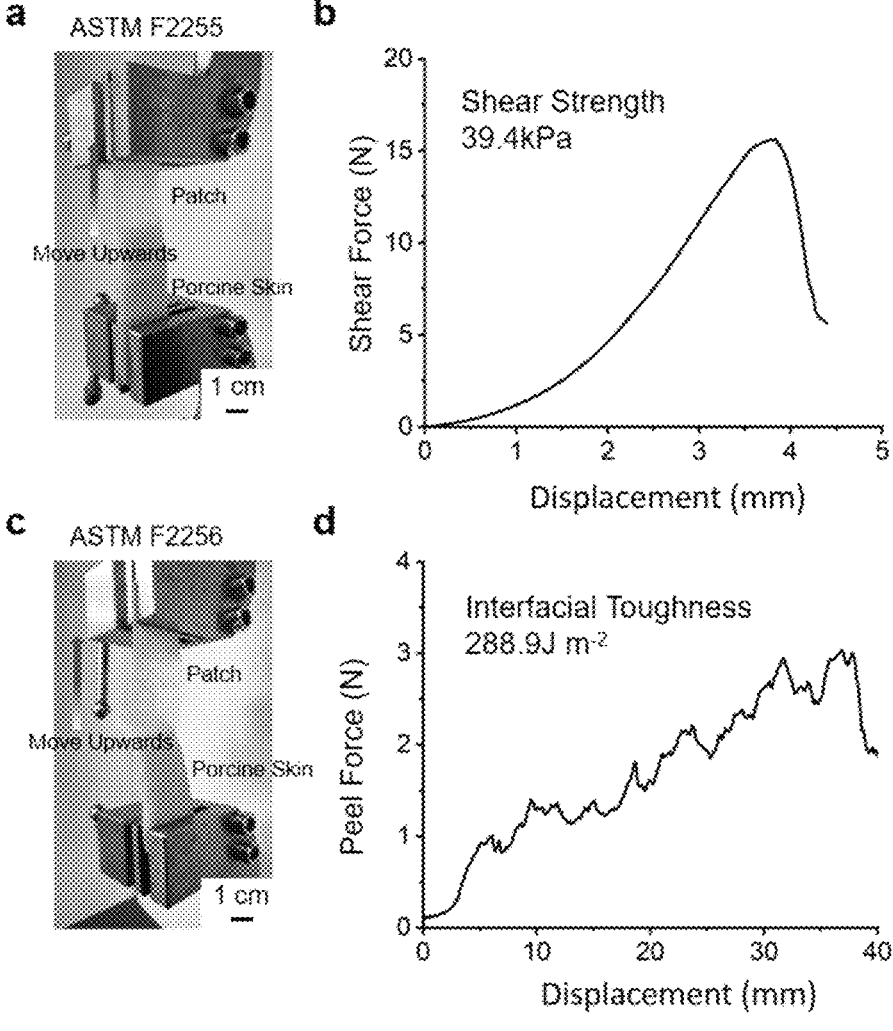
FIG. 3 (a) shows a shear tensile test on tissue adherence conducted by the ASTM F2255 method; (b) shows a shear force-displacement curve of a self-adhesive absorbable biological patch; (c) shows a T peeling test on tissue adherence by the ASTM F2256 method; (d) shows a peel force-displacement curve of a self-adhesive absorbable biological patch.

The self-adhesive absorbable biological patch obtained in Example 1 was used as an experimental sample. With reference to ASTM F2255, fresh dorsal pigskin was defatted and then cut into a size of 5 cm×2.5 cm. The biological patch was also cut into a size of 5 cm×2.5 cm. Thereafter, the biological patch was quickly bonded to one end (with the bond area of 2.5 cm×1 cm) of the pigskin in opposite directions, and fixed at room temperature for 60 min. The free end of the biological patch and the pigskin were stretched at a tensile speed of 5 mm/min at room temperature until they were broken or separated from each other. The force-displacement data were recorded. The force-displacement curve was drawn and analyzed. The maximum shear force ($F_{max}$) was recorded. The shear strength of the biological patch was calculated based on the equation: shear force (Pa)=$F_{max}$(N)/stressed area (m$^2$). The results were as shown in FIG. 3($b$).

Experimental Example 4: Peel Strength Test

The self-adhesive absorbable biological patch obtained in Example 1 was used as an experimental sample. With reference to ATSM F2256, fresh dorsal pigskin was defatted and then cut into a size of 5 cm×2.5 cm. The biological patches were also cut into a size of 5 cm×2.5 cm. Thereafter, the biological patch was quickly bonded to the pigskin (with the bond area of 2.5 cm×1 cm) in the same direction, and fixed at room temperature for 60 min. The free end of the biological patch and the pigskin were stretched at a tensile speed of 5 mm/min at room temperature until they are broken or separated from each other. The force-displacement data were recorded. The force-displacement curve was drawn and analyzed. The maximum shear force ($F_{max}$) was recorded. The interfacial toughness of the biological patch was calculated based on the equation: interfacial toughness (J m$^{-2}$)=2×$F_{max}$(N)/width (m). The results were as shown in FIG. 3 ($d$).

Experimental Example 5: Cytocompatibility Experiment

Figure 4:
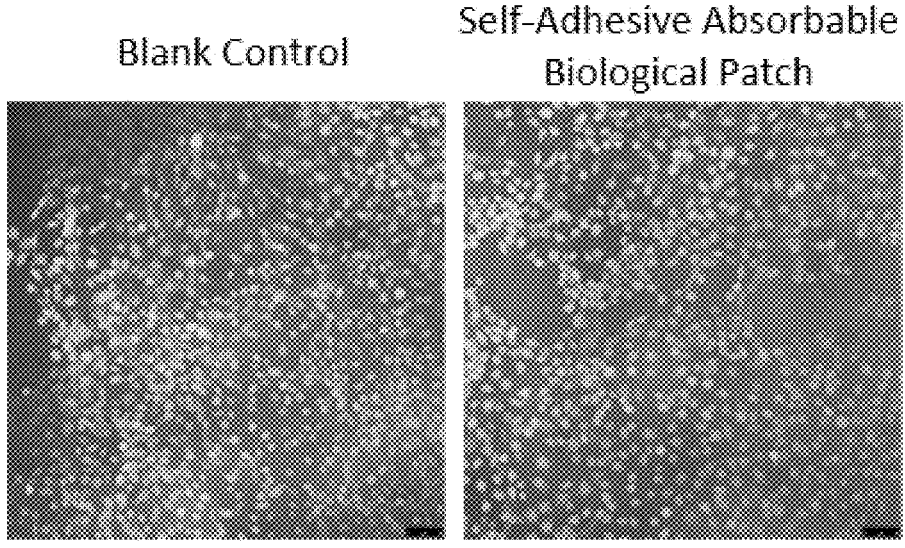
FIG. 4 shows staining diagrams of live and dead cells of mouse fibroblast L929 of the leach liquor of a self-adhesive absorbable biological patch and a blank control.

The self-adhesive absorbable biological patch obtained in Example 1 was used as an experimental sample. The self-adhesive absorbable biological patches were soaked in cell medium at a rate of 6 cm$^2$/mL for 24 h at 37° C. The media formed under these conditions were used to replace common media in 24-well plate inoculated with 10,000 mouse fibroblasts L929 per well. 24 h later, the cells were incubated in the dark for 20 min using a live & dead cell fluorescent dye working solution (calcein-AM/PI), and placed under a laser confocal microscope to observe the state of cells. The results were as shown in FIG. 4. The fluorescence image showed that there was no significant difference in the number of live cells between the self-adhesive absorbable biological patch and the blank control, indicating that this material had good cytocompatibility and could be used as a biomedical material with tissue adhesiveness.

While the embodiments of the present disclosure have been described above, the present disclosure is not limited thereto. Any modifications, equivalent substitutions, improvements, and the like made within the spirit and principle of the present disclosure shall all be encompassed within the scope of protection for the present disclosure.

What is claimed is:

1. A self-adhesive absorbable biological patch, comprising a substrate layer and an adhesive coating located on the substrate layer, wherein the substrate layer is a biological material; the adhesive coating comprises a succinimidyl ester group-grafted polyacrylic crosslinked copolymer, and further comprises an additional biodegradable polymer; and the crosslinked copolymer is formed by polymerizing and crosslinking acrylic acid and/or acrylamide with an acrylated biodegradable polymer and acrylic acid-N-succinimidyl ester.

2. The self-adhesive absorbable biological patch according to claim 1, wherein a weight ratio of acrylic acid and/or acrylamide, the acrylated biodegradable polymer, and acrylic acid-N-succinimidyl ester as three monomers in the crosslinked copolymer is (50 to 300):(2 to 50):(1 to 50), or (200 to 300):(2 to 30):(1 to 20), or (200 to 300):(2 to 10):(1 to 10).

3. The self-adhesive absorbable biological patch according to claim 2, wherein a weight ratio of the crosslinked copolymer to the additional biodegradable polymer in the adhesive coating is (1 to 8):(0 to 3), or (2 to 8):(1 to 3), or (2.7 to 4.3):(1 to 1.5).

4. The self-adhesive absorbable biological patch according to claim 1, wherein an amount of the crosslinked copolymer in the adhesive coating is 4 to 120 mg/cm$^2$, or 10 to 80 mg/cm$^2$, or 20 to 40 mg/cm$^2$.

5. The self-adhesive absorbable biological patch according to claim 4, wherein an amount of the biodegradable polymer in the adhesive coating is 0 to 30 mg/cm$^2$, or 1 to 20 mg/cm$^2$, or 5 to 10 mg/cm$^2$.

6. The self-adhesive absorbable biological patch according to claim 1, wherein the adhesive coating further contains an additional active substance.

7. The self-adhesive absorbable biological patch according to claim 1, wherein the substrate layer is the biological material containing a collagen protein.

8. The self-adhesive absorbable biological patch according to claim 7, wherein the substrate layer is submucosa, dermis, pericardium, collagen, or gelatin.

9. The self-adhesive absorbable biological patch according to claim 7, wherein the substrate layer is decellularized small intestinal submucosa, decellularized dermis or decellularized pericardium;

wherein the substrate layer has a thickness of 0.01 mm to 1 mm, or 0.08 mm to 0.3 mm;

the substrate layer is a homogeneous layer;

the substrate layer is in the form of a laminate formed by two or more separated layers; and/or the substrate layer is composed of 2 to 9 layers of the decellularized small intestinal submucosa.

10. A kit comprising a substrate layer; and the precursor solution mixture according to claim 9, wherein each of the substrate layer and the precursor solution mixture are individually packaged, and wherein the substrate layer is a biological material.

11. A method of preparing a self-adhesive absorbable biological patch according to claim 1, comprising preparing a precursor solution mixture; and coating the precursor solution mixture on the substrate layer in a coating amount of 10 to 300 µL/cm$^2$;

wherein the precursor solution mixture comprises, based on a total mass of the mixture, 5.0 to 30.0 wt. % of acrylic acid and/or acrylamide, 0.2 to 5.0 wt. % of acrylated biodegradable polymer, 0.1 to 5.0 wt. % of acrylic acid-N-succinimidyl ester, 0 to 15.0 wt. % of biodegradable polymer, and a crosslinking amount of crosslinking agent.

12. The method according to claim 11, wherein:

the method further comprises a step of subjecting an adhesive coating to crosslinking treatment to fully polymerize and crosslink the adhesive coating;

the method further comprises subjecting the adhesive coating to dialysis treatment; and/or the method further comprises subjecting the self-adhesive absorbable biological patch to dehydration treatment.

13. A dry adhesive material for bonding a tissue surface, comprising a succinimidyl ester group-grafted polyacrylic crosslinked copolymer, and further comprising a biodegradable polymer; wherein the crosslinked copolymer is formed by polymerizing and crosslinking acrylic acid and/or acrylamide with an acrylated biodegradable polymer and acrylic acid-N-succinimidyl ester.

14. The dry adhesive material according to claim 13, wherein a weight ratio of acrylic acid and/or acrylamide, the acrylated biodegradable polymer, and acrylic acid-N-succinimidyl ester as three monomers in the crosslinked copolymer is (50 to 300):(2 to 50):(1 to 50), or (200 to 300):(2 to 30):(1 to 20), or (200 to 300):(2 to 10):(1 to 10).

15. The dry adhesive material according to claim 13, wherein a weight ratio of the crosslinked copolymer to the biodegradable polymer in the dry adhesive material is (1 to 8):(0 to 3), or (2 to 8):(1 to 3), or (2.7 to 4.3):(1 to 1.5);

wherein an amount of the crosslinked copolymer in the dry adhesive material is 4 to 120 mg/cm$^2$, or 10 to 80 mg/cm$^2$, or 20 to 40 mg/cm$^2$;

an amount of the biodegradable polymer in the dry adhesive material is 0 to 30 mg/cm$^2$, or 1 to 20 mg/cm$^2$, or 5 to 10 mg/cm$^2$; and/or

the dry adhesive material further contains an additional active material.

16. A precursor solution mixture comprising, based on a total mass of the mixture, 5.0 to 30.0 wt. % of acrylic acid and/or acrylamide, 0.2 to 5.0 wt. % of acrylated biodegradable polymer, 0.1 to 5.0 wt. % of acrylic acid-N-succinimidyl ester, 0 to 15.0 wt. % of biodegradable polymer, and a crosslinking amount of crosslinking agent.

17. A kit comprising a substrate layer; and the precursor solution mixture according to claim 9, wherein each of the substrate layer and the precursor solution mixture are individually packaged, and wherein the substrate layer is a biological material.

18. The precursor solution mixture according to claim 16, wherein:

the content of acrylic acid and/or acrylamide is 10.0 to 30.0 wt. %, or 20.0 to 30.0 wt. %;

the content of the acrylated biodegradable polymer is 0.5 to 4.0 wt. %, or 1.0 to 3.0 wt. %;

the content of acrylic acid-N-succinimidyl ester is 0.5 to 3.0 wt. %, or 0.8 to 1.2 wt. %;

the content of the biodegradable polymer is 5.0 to 15.0 wt. %, or 8.0 to 12.0 wt. %; and/or the content of the crosslinking agent is 0.1 to 0.3 wt. %.

* * * * *